US007129277B2

(12) United States Patent
Baran, Jr.

(10) Patent No.: US 7,129,277 B2
(45) Date of Patent: *Oct. 31, 2006

(54) EMULSIONS INCLUDING SURFACE-MODIFIED INORGANIC NANOPARTICLES

(75) Inventor: Jimmie R. Baran, Jr., Prescott, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 268 days.

This patent is subject to a terminal disclaimer.

(21) Appl. No.: 10/335,290

(22) Filed: Dec. 31, 2002

(65) Prior Publication Data

US 2004/0127580 A1    Jul. 1, 2004

(51) Int. Cl.
*B01F 3/08* (2006.01)
*B01F 17/00* (2006.01)

(52) U.S. Cl. .................... 516/22; 423/445 B; 977/734; 977/754

(58) Field of Classification Search .................... 516/22
See application file for complete search history.

(56) References Cited

U.S. PATENT DOCUMENTS

| | | |
|---|---|---|
| 2,801,185 A | 7/1957 | Iler |
| 4,379,201 A | 4/1983 | Heilmann et al. |
| 4,455,205 A | 6/1984 | Olson et al. |
| 4,478,876 A | 10/1984 | Chung |
| 4,486,504 A | 12/1984 | Chung |
| 4,491,508 A | 1/1985 | Olson et al. |
| 4,522,958 A | 6/1985 | Das et al. |
| 4,737,559 A | 4/1988 | Kellen et al. |
| 5,037,579 A | 8/1991 | Matchett |
| 5,258,225 A | 11/1993 | Katsamberis |
| 5,387,617 A | 2/1995 | Hedstrand et al. |
| 5,401,785 A | 3/1995 | Kumagai et al. |
| 5,612,021 A | 3/1997 | Mellul |
| 5,648,407 A | 7/1997 | Goetz et al. |
| 5,879,715 A * | 3/1999 | Higgins et al. ............. 424/489 |
| 6,001,342 A | 12/1999 | Forestier et al. |
| 6,004,567 A * | 12/1999 | Marchi-Lemann et al. . 424/401 |
| 6,020,419 A * | 2/2000 | Bock et al. ................. 524/590 |
| 6,068,835 A | 5/2000 | Franzke et al. |
| 6,126,948 A * | 10/2000 | Simonnet et al. ........... 424/401 |
| 6,177,414 B1 | 1/2001 | Tomalia et al. |
| 6,245,318 B1 | 6/2001 | Klibanov et al. |
| 6,258,896 B1 | 7/2001 | Abuelyaman et al. |
| 6,280,748 B1 | 8/2001 | Morita et al. |
| 6,391,326 B1 | 5/2002 | Crepeau et al. |
| 6,436,424 B1 | 8/2002 | Vogel et al. |
| 6,440,399 B1 | 8/2002 | Gers-Barlag et al. |
| 2002/0128336 A1 | 9/2002 | Kolb et al. |
| 2002/0160030 A1 | 10/2002 | Gers-Barlag et al. |
| 2002/0172716 A1 | 11/2002 | Walt et al. |
| 2003/0165553 A1 | 9/2003 | Gers-Barlag et al. |
| 2003/0228339 A1 | 12/2003 | El-Nokaly et al. |
| 2004/0067208 A1 | 4/2004 | Lennon et al. |

FOREIGN PATENT DOCUMENTS

| | | |
|---|---|---|
| EP | 0 608 908 A2 | 8/1994 |
| EP | 1 057 841 A2 | 12/2000 |
| EP | 1 017 745 B1 | 5/2001 |
| JP | 6-242543 | 9/1994 |
| JP | 2001-348214 A | 12/2001 |
| WO | WO 00/06495 | 2/2000 |
| WO | WO 01/85324 A1 | 11/2001 |

OTHER PUBLICATIONS

Mill et al., "Emulsion", in AccessScience@McGraww-Hill, http://www.accessscience.com, DOI 10.1036/1097-8542.231100, last modified: Apr. 10, 2000.*
M.Samy El-Shall, "Nanoparticles", in AccessScience@McGraw-Hill, http://www.accessscience.com, DOI 10.1036/1097-8542.YB031425, last modified: Dec. 23, 2002.*
U.S. Appl. No. 10/334,963, filed Dec. 31, 2002, Stabilized Foams Including Surface-Modified Organic Molecules.
U.S. Appl. No. 10/335,495, filed Dec. 31, 2002, Emulsions Including Surface-Modified Organic Molecules.
Website Article: Dendritech®, Inc., "Current Applications", http://www.dendritech.com/applications.html. Aug. 29, 2002.
Website Article: Dendritech®, Inc., "PAMAM Denrimers". http://www.dendriech.com/pamam.html. Aug. 29, 2002.
Website Article: Dendritech®, Inc., "Pricing & Ordering Information", http://www.dendritech.com/pricing.html, Aug. 29, 2002.
"DISPERSANTS", Encyclopedia of Chemical Technology. Fouth Edition. Kirk-Othmer, vol. 8, Deuterium and Tritium to Elastomers, Polyethers, 1993, pp. 293-311.
Fisher et al., "Effect of Silica Nanoparticle Size on the Stability of Alumina/Silica Suspensions", J. Am. Comm. Soc., 84{4}, pp. 713-718, 2001.
"EMULSIONS", Encyclopedia of Chemical Technology, Fourth Edition, Kirk-Othmer, vol. 9, Elastomers, Polyisoprene To Expert Systems, 1994, pp. 393-413.
"FOAMS", Encyclopedia of Chemical Technology, Fourth Edition, Kirk-Othmer, vol. 11, Flavor Characterization To Fuel Cells, 1994, pp. 783-805.
Tohver et al., "Nanoparticle Engineering of Complex Fluid Behavior", Langmuir 2001, 17, pp. 8414-8421.
Wasan et al., "New Vistas in Dispersion Science and Engineering", AIChe Journal, Mar. 2003, vol. 49, No. 3 pp. 550-556.
Website Article: Jacoby, "Nanoparticles Stabilize Colloids", Chemical & Engineering News, http://pubs.acs.org/cen/topstory/8001/8001notw8.html, Nov. 14, 2002.
"Nanotechnology could save the ozone layer", nanotechweb.org, Jan. 30, 2003.
Binks, "Particles as surfactants—similarities and differences", ELSEVIER, Current Opinion in Colloid & Interface Science 7 (2002). pp. 21-41.

* cited by examiner

*Primary Examiner*—Randy Gulakowski
*Assistant Examiner*—Timothy J. Kugel

(57) ABSTRACT

The invention is related to emulsions containing surface-modified inorganic nanoparticles.

19 Claims, No Drawings

EMULSIONS INCLUDING SURFACE-MODIFIED INORGANIC NANOPARTICLES

BACKGROUND

The present invention relates to stabilized liquid-in-liquid dispersions or emulsions.

Traditional emulsions are made up of two phases: a dispersed phase and a continuous phase. The most common emulsions consist of only two liquids, water and oil. An o/w (oil-in-water) emulsion consists of oil droplets dispersed in a continuous aqueous phase, and a w/o (water-in-oil) emulsion consists of water droplets dispersed in oil. Multiple emulsions may be formed, for example, when water droplets in a continuous oil phase themselves contain dispersed oil droplets. Emulsification consists of the break-up of large droplets into smaller droplets due to shear forces. Typically, emulsifiers are used to stabilize emulsions through a reduction in interfacial tension. Increasing the viscosity of the continuous phase may also prevent phase separation of emulsions.

SUMMARY

In one aspect, the invention provides an emulsion that comprises a liquid continuous phase comprising surface-modified inorganic molecules having an individual particle diameter of less than about 100 nanometers, and a dispersed liquid phase.

In other embodiments, the emulsions of the invention are free of surfactant or free of compounds that reduce surface tension.

DETAILED DESCRIPTION

The emulsions of the invention are liquid-in-liquid dispersions. The emulsions comprising a continuous phase and a dispersed phase are maintained by incorporation of an effective amount of surface-modified nanoparticles into the composition. The surface-modified nanoparticles stabilize the emulsion without reducing surface tension at the continuous-dispersed phase interface.

In another embodiment, the emulsions of the invention consist essentially of a continuous liquid phase and a dispersed liquid phase and surface-modified inorganic nanoparticles incorporated in the continuous phase.

The emulsions of the invention may be free of traditional surfactants, detergents, proteins, and emulsifiers and other compounds that stabilize emulsions through a reduction in surface tension. The emulsions of the invention are typically stable from days to years under constant temperature.

The emulsions of the invention may be oil-in-water or water-in-oil emulsions (as those terms are generally defined in the art) or multiple emulsions. An example of a multiple emulsion is an oil-in-water emulsion (dispersed phase) in an oil continuous phase or the opposite multiple emulsion. For multiple emulsions of the invention, different types of surface-modified organic molecules or organic polymeric microspheres are or may be needed for each phase that contains another dispersed phase.

The surface-modified nanoparticles stabilize emulsions without lowering the surface tension at the interface between the dispersed and continuous phases. It is theorized that the surface-modified nanoparticles become situated between the dispersed phase droplets in increasing concentration as the liquid continuous phase drains from between the dispersed phase droplets. The increased concentration of surface-modified nanoparticles between the dispersed phase droplets prevents the dispersed droplets from contacting one another and coalescing.

Examples of liquid continuous phases include water, organic liquids including, e.g., acids, alcohols, ketones, aldehydes, amines, amides, esters, glycols, ethers, hydrocarbons, halocarbons, monomers, oligomers, lubricating oils, vegetables oils (including mono- di, and tri-glycerides), silicone oils, moisturizing oils (e.g., mineral and jojoba oils), fuel oils, fuels (including kerosene, gasoline, diesel fuel), oligomers of ethylene glycol, alkyl and aryl nitro compounds, partially or fully fluorinated compounds, and polymers.

Stabilized emulsions of the invention include surface-modified inorganic nanoparticles. The surface-modified nanoparticles are typically individual, unassociated (i.e., non-aggregated) nanoparticles dispersed throughout the continuous phase and preferably do not irreversibly associate with each other. The term "associate with" or "associating with" includes, for example, covalent bonding, hydrogen bonding, electrostatic attraction, London forces, and hydrophobic interactions.

The surface-modified nanoparticles are selected such that the composition formed therewith is free from a degree of particle agglomeration or aggregation that would interfere with the desired properties of the composition. The surface-modified nanoparticles are selected to be compatible with the continuous phase.

One useful method of assessing the compatibility of the surface-modified nanoparticles with the continuous phase includes the step of combining the surface-modified nanoparticles and the continuous phase and observing whether the surface-modified nanoparticles appear to dissolve in the continuous phase.

The nature of the inorganic particle component of the surface-modified particle will prevent the surface-modified particle from actually dissolving in the continuous phase, i.e., the surface-modified nanoparticles will be dispersed in the continuous phase, however, the compatibility of the surface groups with the continuous phase will give the surface-modified nanoparticles the appearance of dissolving in the continuous phase. As the size of the surface-modified nanoparticles increases, the haziness of the continuous phase generally increases. Preferred surface-modified nanoparticles are selected such that they do not settle out of the continuous phase. The further step in assessing the compatibility of the continuous phase and the surface-modified nanoparticles includes determining whether, upon subsequent introduction of liquid to be dispersed in the continuous phase, the composition forms a stable emulsion.

Suitable surface groups can also be selected based upon the solubility parameter of the surface group and the continuous phase. Preferably, the surface group, or the agent from which the surface group is derived, has a solubility parameter similar to the solubility parameter of the continuous phase. When the continuous phase is hydrophobic, for example, one skilled in the art can select from among various hydrophobic surface groups to achieve a surface-modified particle that is compatible with the hydrophobic continuous phase. Similarly, when the continuous phase is hydrophilic, one skilled in the art can select from hydrophilic surface groups, and, when the continuous phase is a fluorocarbon, one skilled in the art can select from among various compatible surface groups. The nanoparticle can also include at least two different surface groups that combine to provide a nanoparticle having a solubility parameter that is similar to the solubility parameter of the continuous phase. The surface-modified nanoparticles are not amphiphilic.

The surface groups may be selected to provide a statistically averaged, randomly surface-modified particle.

The surface groups are present on the surface of the particle in an amount sufficient to provide surface-modified nanoparticles that are capable of being subsequently dispersed in the continuous phase without aggregation. The surface groups preferably are present in an amount sufficient to form a monolayer, preferably a continuous monolayer, on the surface of the nanoparticle.

Surface-modifying groups may be derived from surface-modifying agents. Schematically, surface-modifying agents can be represented by the formula A-B, where the A group is capable of attaching to the surface of the particle and the B group is a compatibilizing group that may be reactive or non-reactive with a component of the continuous phase. Compatibilizing groups can be selected to render the particle relatively more polar, relatively less polar, or relatively non-polar.

Suitable classes of surface-modifying agents include, e.g., silanes, organic acids, organic bases, and alcohols.

Particularly useful surface-modifying agents include silanes. Examples of useful silanes include organosilanes including, e.g., alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris(isopropenoxy)silane and vinyltris(2-methoxyethoxy)silane; trialkoxyarylsilanes; isooctyltrimethoxy-silane; N-(3-triethoxysilylpropyl) methoxyethoxyethoxy ethyl carbamate; N-(3-triethoxysilylpropyl) methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane, and 3-(methacryloyloxy)propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Methods of surface-modifying silica using silane functional (meth)acrylates are described, e.g., in U.S. Pat. Nos. 4,491,508 and 4,455,205 (Olsen et al.); U.S. Pat. Nos. 4,478,876 and 4,486,504 (Chung); and U.S. Pat. No. 5,258,225 (Katsamberis), and incorporated herein.

Useful organic acid surface-modifying agents include, e.g., oxyacids of carbon (e.g., carboxylic acid), sulfur and phosphorus, and combinations thereof.

Representative examples of polar surface-modifying agents having carboxylic acid functionality include $CH_3O(CH_2CH_2O)_2CH_2COOH$ ([2-(2-methoxy-ethoxy)-ethoxy] acetic acid, hereafter MEEAA) and 2-(2-methoxyethoxy) acetic acid having the chemical structure $CH_3OCH_2CH_2OCH_2COOH$ (hereafter MEAA) and mono (polyethylene glycol) succinate.

Representative examples of non-polar surface-modifying agents having carboxylic acid functionality include octanoic acid, dodecanoic acid, and oleic acid.

Examples of suitable phosphorus containing acids include phosphonic acids including, e.g., octylphosphonic acid, laurylphosphonic acid, decylphosphonic acid, dodecylphosphonic acid, and octadecylphosphonic acid.

Useful organic base surface-modifying agents include, e.g., alkylamines including, e.g., octylamine, decylamine, dodecylamine, and octadecylamine.

Examples of other useful non-silane surface-modifying agents include acrylic acid, methacrylic acid, beta-carboxyethyl acrylate, mono-2-(methacryloyloxyethyl) succinate, and combinations thereof. A useful surface-modifying agent that imparts both polar character and reactivity to the nanoparticles is mono(methacryloyloxypolyethyleneglycol) succinate.

Examples of suitable surface-modifying alcohols include, e.g., aliphatic alcohols including, e.g., octadecyl, dodecyl, lauryl and furfuryl alcohol, alicyclic alcohols including, e.g., cyclohexanol, and aromatic alcohols including, e.g., phenol and benzyl alcohol, and combinations thereof.

When the continuous phase includes aromatic ring containing epoxy resins, useful surface-modifying groups can include an aromatic ring. Examples of surface-modifying groups particularly suitable for epoxy resin compositions are disclosed in U.S. Pat. No. 5,648,407 (Goetz et al.) and incorporated herein.

A variety of methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. Nos. 2,801,185 (Iler) and 4,522,958 (Das et al.), and incorporated herein.

The nanoparticles are inorganic. Examples of suitable inorganic nanoparticles include silica and metal oxide nanoparticles including zirconia, titania, ceria, alumina, iron oxide, vanadia, antimony oxide, tin oxide, alumina/silica, and combinations thereof. The nanoparticles have an average particle diameter less than about 100 nm; no greater than about 50 nm; from about 3 nm to about 50 nm; from about 3 nm to about 20 nm; or from about 3 nm to about 10 nm. The nanoparticles used in the emulsions of the invention are typically un-aggregated. If the nanoparticles are aggregated, the maximum cross-sectional dimension of the aggregated particle is within any of these preferable ranges.

Useful surface-modified zirconia nanoparticles include zirconia nanoparticles surface modified with organic acids, for example, oleic acid and acrylic acid adsorbed onto the surface of the particle.

Useful surface-modified silica nanoparticles include silica nanoparticles surface-modified with silane surface-modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface-modifying agents including, e.g., alcohol, organosilane including, e.g., alkyltrichlorosilanes, trialkoxyarylsilanes, trialkoxy(alkyl)silanes, and combinations thereof and organotitanates and mixtures thereof.

The nanoparticles may be in the form of a colloidal dispersion. Examples of useful commercially available unmodified silica starting materials include nano-sized colloidal silicas available under the product designations NALCO 1040, 1050, 1060, 2326, 2327, and 2329 colloidal silica from Nalco Chemical Co., Naperville, Ill.

Useful metal oxide colloidal dispersions include colloidal zirconium oxide, suitable examples of which are described in U.S. Pat. No. 5,037,579 and incorporated herein, and colloidal titanium oxide, useful examples of which are described in PCT Publication No. WO 00/06495, entitled, "Nanosize Metal Oxide Particles for Producing Transparent Metal Oxide Colloids and Ceramers," (Arney et al.), filed Jul. 30, 1998, and incorporated herein.

The emulsions of the invention have a liquid dispersed phase that is dispersed within the continuous liquid phase. The liquid dispersed phase may comprise one or more liquids that are miscible or soluble and that are dispersed within the liquid continuous phase. Examples of suitable liquid dispersed phases include water and all of the organic materials listed above for use as a continuous phase.

Each phase may also contain other dissolved or soluble compounds or components which are added to achieve a desired effect, for example, salts, drugs, dyes, flame retardants, and the like.

The emulsions of the invention may also contain surface-modified organic molecules and organic polymeric microspheres in combination with surface-modified inorganic nanoparticles. Surface-modified organic molecules and organic polymeric microspheres are described in U.S. Patent Publication No. 2004/0127612 A1, incorporated herein by reference for the description of the surface-modified organic molecules and organic polymeric microspheres.

The emulsions of the invention are generally made by blending the phases and mixing. Another way to make the emulsions of the invention is to blend the surface-modified organic molecules or organic polymeric microspheres or combinations thereof with the continuous phase (or other phases in the case of multiple emulsions) and then adding the dispersed phase with agitation.

The emulsions of the invention may be useful in foods, cosmetics, pharmaceuticals, and the like.

The invention will now be described further by way of the following examples.

EXAMPLES

All solvents and reagents were obtained from Aldrich Chemical Company, Milwaukee, Wis., unless otherwise noted. All percents and amounts are by weight unless otherwise specified.

Preparation of Poly(Alkylene Oxide) Substituted Silica Nanoparticles (Silica-1230)

A mixture of 100 g of NALCO 2326 colloidal silica (available from Nalco Chemical Co.), 100 g of water and 19.82 g of gamma-poly(alkylene oxide)propyl trimethoxysilane (obtained from OSi Specialties, Inc., Endicott, N.Y., under the trade designation of SILQUEST A-1230) was heated in a sealed glass jar in an oven at 80° C. for 18 hours. The product was used without further purification.

Preparation of Iso-Octyl Substituted Silica Nanoparticles (i-$C_8$-silica)

Iso-Octyl substituted silica nanoparticles were prepared as described in U.S. Pat. Publication No. 2002/0128336, incorporated herein by reference, for the preparation of the surface-modified nanoparticles.

Example 1

An emulsion of toluene and fluorocarbon (FLUORINERT FC-75, available from 3M Company, St. Paul, Minn.) was prepared by combining in a screw-cap glass vial 1 mL of FLUORINERT FC-75 and 1 mL of a 2% mixture of i-$C_8$-silica and toluene and shaking the vial vigorously by hand for 15 seconds. The emulsion comprised less than 50 volume percent toluene, as evidenced by the separation of a homogeneous toluene phase from the emulsion phase.

Example 2

A multiple emulsion comprising predominately an emulsion of water in toluene which was itself emulsified in water was prepared by combining in a vial a mixture of 5 g of 0.5% i-$C_8$-silica in toluene, and 5 g of 1.5% of Silica-1230 in water. The mixture was stirred for 5 minutes with a SILVERSON model L2R mixer (available from Silverson Machines Inc., East Longmeadow, Mass.), fitted with a ⅝-inch tubular assembly disintegrating head impeller to afford a cloudy liquid. The liquid was analyzed by optical microscopy and was found to be predominately the multiple emulsion of water-in-toluene-in-water.

Example 3

A multiple emulsion comprising predominately an emulsion of toluene in water which was itself emulsified in toluene was prepared by combining in a vial a mixture of 5 g of 1.5% i-$C_8$-silica in toluene and 5 g of 0.5% Silica-1230 in water. The mixture was stirred for 5 minutes with a SILVERSON model L2R mixer (available from Silverson Machines Inc.), fitted with a ⅝-inch tubular assembly disintegrating head impeller to afford a cloudy liquid. The liquid was analyzed by optical microscopy and was found to be predominately the multiple emulsion of toluene-in-water-in-toluene.

Example 4

A multiple emulsion comprising predominately an emulsion of fluorocarbon (FLUORINERT FC-75) in toluene which was itself emulsified in water was prepared by combining in a vial a mixture of 1 g FLUORINERT FC-75, 5 g of a mixture of 1.5% Silica-1230 in water and 4 g of a mixture of 0.5% i-C8-silica in toluene. The mixture was stirred for 5 minutes with a SILVERSON model L2R mixer (available from Silverson Machines Inc.), fitted with a ⅝-inch tubular assembly disintegrating head impeller to afford a cloudy liquid. The liquid was analyzed by optical microscopy and was found to be predominately the multiple emulsion of FLUORINERT FC-75-in-toluene-in-water.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. An emulsion comprising:
   a continuous liquid phase comprising a plurality of surface modified inorganic nanoparticles having a particle diameter of less than about 100 nanometers and surface-modified organic molecules selected from the group consisting of surface-modified fullerenes and surface modified dendrimers, or organic polymeric microspheres comprising polystyrene, or a combination thereof dispersed in said continuous phase; and
   a dispersed liquid phase dispersed in said continuous phase.

2. The emulsion of claim 1 wherein said individual nanoparticles have a particle diameter no greater than about 50 nanometers.

3. The emulsion of claim 1 wherein said individual nanoparticles have a particle diameter in the range of from about 3 nanometers to about 50 nanometers.

4. The emulsion of claim 1 wherein said individual nanoparticles have a particle diameter of no greater than about 20 nanometers.

5. The emulsion of claim 1 wherein said individual nanoparticles have a particle diameter in the range of from about 3 nanometers to about 20 nanometers.

6. The emulsion of claim 1 wherein said individual nanoparticles have a particle diameter in the range of from about 3 nanometers to about 10 nanometers.

7. The emulsion of claim 1 wherein said nanoparticles are selected from the group consisting of silica, titania, alumina, zirconia, vanadia, ceria, iron oxide, antimony oxide, tin oxide, alumina/silica, and combinations thereof.

8. The emulsion of claim 1 wherein said nanoparticles comprise surface groups selected from the group consisting of hydrophobic groups, hydrophilic groups, and combinations thereof.

9. The emulsion of claim 1 wherein said nanoparticles comprise surface groups derived from an agent selected from the group consisting of silane, organic acid, organic base, and combinations thereof.

10. The emulsion of claim 1 wherein said nanoparticles comprise organosilyl surface groups derived from an agent selected from the group consisting of alkylsilane, arylsilane, alkoxysilane, and combinations thereof.

11. The emulsion of claim 1 wherein said nanoparticles comprise surface groups derived from an agent selected from the group consisting of carboxylic acids, sulfonic acids, phosphonic acids, and combinations thereof.

12. The emulsion of claim 1 wherein the continuous phase is selected from the group consisting of water, organic acids, alcohols, ketones, aldehydes, amines, amides, esters, glycols, ethers, hydrocarbons, halocarbons, monomers, oligomers, lubricating oils, vegetable oils, silicone oils, mineral and jojoba oils, fuel oils, kerosene, gasoline, diesel fuel, oligomers of ethylene glycol, alkyl and aryl nitro compounds, partially or fully fluorinated compounds, polymers, and combinations thereof.

13. The emulsion of claim 1 wherein the dispersed phase is selected from the group consisting of water, organic acids, alcohols, ketones, aldehydes, amines, amides, esters, glycols, ethers, hydrocarbons, halocarbons, monomers, oligomers, lubricating oils, vegetable oils, silicone oils, mineral and jojoba oils, fuel oils, kerosene, gasoline, diesel fuel, oligomers of ethylene glycol, alkyl and aryl nitro compounds, partially or fully fluorinated compounds, polymers, and combinations thereof.

14. The emulsion of claim 1 dispersed within a second continuous phase.

15. The emulsion of claim 1 free of surfuctant.

16. The emulsion of claim 1 free of compounds that reduce surface tension.

17. The emulsion of claim 1 wherein the continuous phase is water.

18. The emulsion of claim 1 wherein the continuous phase is organic.

19. The emulsion of claim 1 wherein dispersed phase is water.

* * * * *

UNITED STATES PATENT AND TRADEMARK OFFICE
CERTIFICATE OF CORRECTION

PATENT NO. : 7,129,277 B2
APPLICATION NO. : 10/335290
DATED : October 31, 2006
INVENTOR(S) : Jimmie R. Baran, Jr.

Page 1 of 1

It is certified that error appears in the above-identified patent and that said Letters Patent is hereby corrected as shown below:

Title page,
Item (56), References Cited, OTHER PUBLICATIONS, delete "Website Article: Dendritech®, Inc., "PAMAM Denrimers", http://www.dendriech.com/pamam.html, Aug. 29, 2002." and insert in place thereof -- Website Article: Dendritech®, Inc., "PAMAM Dendrimers", http://www.dendritech.com/pamam.html, Aug. 29, 2002. --.

Item (56), References Cited, OTHER PUBLICATIONS, delete ""DISPERSANTS", Encyclopedia of Chemical Technology, Fouth Edition, Kirk-Othmer, vol. 8, Deuterium and Tritium to Elastomers, Polyethers, 1993, pp. 293-311." and insert in place thereof -- ""DISPERSANTS", Encyclopedia of Chemical Technology, Fourth Edition, Kirk-Othmer, vol. 8, Deuterium and Tritium to Elastomers, Polyethers, 1993, pp. 293-311.

Item (56), References Cited, OTHER PUBLICATIONS, delete "Wasan et al., "New Vistas in Dispersion Science and Engineering", AIChe Journal, Mar. 2003, vol. 49, No. 3 pp. 550-556." and insert in place thereof -- Wasan et al., "New Vistas in Dispersion Science and Engineering", AIChE Journal, Mar. 2003, vol. 49, No. 3 pp. 550-556. --

Column 8,
Line 29, delete "surfuctant" and insert in place thereof -- surfactant --.

Signed and Sealed this

Seventeenth Day of April, 2007

JON W. DUDAS
*Director of the United States Patent and Trademark Office*